United States Patent
Ogura et al.

(10) Patent No.: US 7,715,012 B2
(45) Date of Patent: *May 11, 2010

(54) SENSOR UNIT AND ASSAY METHOD OF ASSAY IN UTILIZING ATTENUATED TOTAL REFLECTION

(75) Inventors: Nobuhiko Ogura, Kanagawa (JP); Hitoshi Shimizu, Kanagawa (JP); Koji Kuruma, Kanagawa (JP); Hisashi Ohtsuka, Kanagawa (JP); Tatsuo Fujikura, Kanagawa (JP); Shu Sato, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/394,298

(22) Filed: Feb. 27, 2009

(65) Prior Publication Data
US 2009/0195784 A1 Aug. 6, 2009

Related U.S. Application Data

(63) Continuation of application No. 11/367,302, filed on Mar. 6, 2006, now Pat. No. 7,515,270.

(30) Foreign Application Priority Data
Mar. 7, 2005 (JP) .............................. 2005-062901

(51) Int. Cl.
*G01N 21/55* (2006.01)
(52) U.S. Cl. ..................................................... 356/445
(58) Field of Classification Search ...................... None
See application file for complete search history.

(56) References Cited

FOREIGN PATENT DOCUMENTS

| JP | 6-167443 A | 6/1994 |
|---|---|---|
| WO | 97/01087 | 1/1997 |
| WO | 00/07008 | 2/2000 |

*Primary Examiner*—Gregory J Toatley, Jr.
*Assistant Examiner*—Amanda H Merlino
(74) *Attorney, Agent, or Firm*—Sughrue Mion, PLLC

(57) ABSTRACT

A sensor unit of a surface plasmon resonance (SPR) assay system includes a transparent dielectric medium. A thin film has a first surface and a sensing surface. The first surface is connected with the dielectric medium to constitute an interface. The sensing surface is back to the first surface, for detecting (bio) chemical reaction. A flow cell block has a flow channel for flowing of the sample to the sensing surface. Attenuated total reflection of illuminating light is checked at the interface, to analyze interaction between ligand and analyte as samples. The flow channel includes a first inner surface, disposed opposite to the sensing surface to extend along, for passing the sample to flow between. The first inner surface has a height, defined with reference to the sensing surface, and in a range of 200-500 microns.

2 Claims, 7 Drawing Sheets

SENSOR UNIT AND ASSAY METHOD OF ASSAY IN UTILIZING ATTENUATED TOTAL REFLECTION

CROSS REFERENCE TO RELATED APPLICATIONS

This is a continuation of application Ser. No. 11/367,302 filed Mar. 6, 2006, which claims benefit of Japanese Application No. 2005-062901 filed Mar. 7, 2005, the entire disclosures of which are incorporated herein by reference.

BACKGROUND OF THE INVENTION

1. Field of the Invention

The present invention relates to a sensor unit and assay method of assay in utilizing attenuated total reflection. More particularly, the present invention relates to a sensor unit and assay method of assay in utilizing attenuated total reflection, in which a flow channel is constructed for assay with high precision.

2. Description of the Related Art

An assay apparatus for assay in utilizing attenuated total reflection is used for various kinds of studies in a biochemical field or the like, for example to study interaction of protein, DNA and various biomaterials, and to select candidate drugs by screening. Also, the technique is useful in the fields of the clinical medicine, food industries and the like.

A surface plasmon resonance (SPR) sensor is known as an assay apparatus in utilizing attenuated total reflection. A thin film/dielectric interface of a metal film is fitted on a dielectric block. Light is directed to the thin film/dielectric interface in a manner conditioned for total reflection. Surface plasmon is a term to mean the compressional wave created on the surface of the metal and included in plasmon as quantized expression of the compressional wave. Free electrons in a metal vibrate to generate the compressional wave.

In the assay apparatus, the sensing surface is positioned opposite to the interface where the metal thin film is connected with the dielectric block. The sensing surface is caused to create surface plasmon resonance. Reaction of samples is assayed by detecting the SPR on the sensing surface.

Illuminating light is applied to an interface between the thin film and the prism or a surface back to the sensing surface at an angle of incidence equal to or more than a critical angle to satisfy a condition of total reflection. Then total reflection of the illuminating light occurs. Upon the total reflection created on the metal/dielectric interface, a small component of the light passes through the metal film without reflection, and penetrates to the sensing surface. A wave of the penetrating component is called an evanescent wave. Surface plasmon resonance (SPR) is created when frequency of the evanescent wave coincides with that of the surface plasmon. In response to this, intensity of the reflected light attenuates remarkably. In the assay apparatus, the attenuation in the reflected light reflected by the metal/dielectric interface is detected, to recognize creation of the SPR on the sensing surface.

A resonance angle or an angle of incidence of light for creation of surface plasmon resonance depends upon a refractive index of a medium of transmission of evanescent waves and surface plasmon. In other words, a change in the refractive index of the medium of transmission causes a change in the resonance angle of creation of SPR. The substance or sample in contact with the sensing surface is the medium for transmitting the evanescent waves and surface plasmon. When binding, dissociation or other reaction occurs on the sensing surface between two molecules or samples, the resonance angle changes because of a change in the refractive index of the medium of transmission. The SPR assay apparatus finds the changes in the resonance angle, to assay the interaction between the molecules or samples.

An assay apparatus for assay in utilizing attenuated total reflection is used for various kinds of studies in a biochemical field or the like, for example to study interaction of protein, DNA and various biomaterials, and to select candidate drugs by screening. Also, the technique is useful in the fields of the clinical medicine, food industries and the like. A sample or biomaterial, such as protein, is handled as sample fluid for the purpose of preventing deactivation or modification due to drying. The sample fluid contains biomaterial and fluid medium, examples of which include pure water, physiological saline water, liquid buffer and the like.

JP-A 6-167443 discloses an SPR assay apparatus in which an optical system of Kretschmann configuration is used for incidence of light to the metal film. According to the Kretschmann configuration, the thin film/dielectric interface of the metal film is fitted on a prism, which condenses light and directs the light to the thin film/dielectric interface in a manner conditioned for total reflection. A sensing surface is overlaid inside the flow channel, for immobilizing the sample. Ligand fluid is introduced to the flow channel for immobilizing the ligand on the sensing surface. After this, analyte fluid is introduced for contact of the analyte and the ligand, to assay the interaction between those.

In JP-A 6-167443, a body of the assay apparatus has a prism and an assay stage loadable with a flow cell block having a flow channel. A chip type of sensor unit is set on the assay stage, the chip type having a transparent glass substrate of a dielectric material, and a thin film overlaid thereon. The chip type of the sensor unit is removable from the body of the apparatus, to set the flow channel at the sensing surface and to fit a surface of the thin film on the prism as an interface. Prior to the assay, there is a process of immobilizing a ligand on the thin film in the sensor unit of the chip type. In JP-A 6-167443, the sensor unit of the chip type is kept located on the assay stage also in the sample immobilizing flow process.

In the flow cell block is formed a flow cell recess, which is set opposite to the sensing surface, and causes a flow of fluid on the sensing surface by contacting ligand or analyte in the fluid with the sensing surface. A confronting portion or retraction portion of the flow channel is constituted by the flow cell recess. In relation to a chip type of sensor unit, the sensing surface externally appears. When the sensor unit is loaded on an assay stage, the retraction portion is hermetically closed by closing an open portion of the flow channel with the sensing surface. Then delivery of the sample fluid to the sensing surface is enabled.

Then the ligand is introduced to the flow channel for the sample immobilizing flow. After this, cleaning liquid is introduced to the flow channel for washing. Before introducing the cleaning liquid, fluid of the ligand has been filled in the flow channel. The cleaning liquid is forcibly delivered despite the ligand. The fluid of the ligand is pushed by the cleaning liquid and flows out of the flow channel. This is substitution of fluids in the flow channel by changing over the content.

After washing, the flow channel is supplied with the buffer liquid and then the analyte fluid, for conducting an assay. At a lapse of a predetermined time, the buffer liquid is introduced again to complete the assay. The buffer liquid is introduced for the purpose of detecting a base line of the output of the SPR. Acquisition of the output is started when the flow channel is filled with the buffer liquid, and is ended upon draining the analyte fluid by flowing again of the buffer liquid. Then the interaction of the analyte and ligand from the association until the dissociation can be detected.

To raise the sample amount of an immobilized ligand to the sensing surface, it is effective to increase the sample amount of an introduced ligand to the flow channel. A volume of the flow channel must be greater by enlarging an area of a section of the flow channel at the retraction portion before the sample amount of the introduced ligand can be greater. Assuming that a channel width of the flow channel is constant, the area of the section is determined by the height of depth of the flow channel from the sensing surface to the upper surface of the flow channel. Consequently, a greater height or depth of the flow channel is preferable.

For the purpose of detecting a reaction speed of samples by the surface plasmon resonance system, the height of the flow channel should be small because of short time of reaction of binding or dissociation of the ligand with the analyte. In general, a fluid flows in the flow channel in such a manner that a gradient in the speed occurs from the center of the flow channel in its section toward the inner surface of the flow channel due to viscosity of the fluid. The speed is lower according to closeness to the inner surface. In operation of substitution of the buffer for the analyte, there is a delay in the sensing surface for the substitution in comparison with the center of the flow channel. A small portion of the analyte remains on the sensing surface. Note that a quantitative level of the residual analyte is represented by a parameter of a ratio of substitution of the flow channel. Note that the ratio of substitution is such of an amount of substituting fluid to the preceding fluid amount of the flow channel. The ratio of substitution rises if the introduction of fluid is repeated for a number of times, or if considerable time is taken for waiting. However, the ratio of substitution of a high level at a short time by introduction at one time is required for accurately measuring the reaction speed. If a height of the flow channel is lowered, a distance from the center of the flow channel to the sensing surface is shortened. The ratio of substitution at a high ratio of substitution in a short time can be obtained by reducing a gradient in the speed due to the fluid viscosity.

The channel height of the flow channel should be conditioned differently between the processes of the sample immobilizing flow and assay. No known technique suggests an optimization of the channel height determined suitably for both of the sample immobilizing flow and assay.

SUMMARY OF THE INVENTION

In view of the foregoing problems, an object of the present invention is to provide a sensor unit and assay method of assay in utilizing attenuated total reflection, in which a flow channel is constructed for assay with high precision.

In order to achieve the above and other objects and advantages of this invention, a sensor unit for assay in utilizing attenuated total reflection is provided, including a transparent dielectric medium, a thin film having a first surface and a sensing surface, the first surface being connected with the dielectric medium to constitute an interface, the sensing surface being back to the first surface, for detecting reaction of a sample, and a flow cell block having a flow channel for flowing of the sample to the sensing surface, wherein illuminating light is applied through the dielectric medium to the interface to satisfy a total reflection condition, and a reflection angle upon occurrence of the attenuated total reflection of the illuminating light changes according to reaction of the sample on the sensing surface. In the sensor unit, the flow channel includes a facing portion, disposed opposite to the sensing surface to extend along, for passing the sample to flow between, the inner surface of the facing portion having a height, defined with reference to the sensing surface, and equal to or more than 200 microns, and equal to or less than 500 microns.

Preferably, the flow cell block has a flow cell recess, and the first inner surface is defined inside the flow cell recess.

Preferably, the height of the first inner surface is equal to or more than 250 microns.

Preferably, the height of the first inner surface is equal to or less than 350 microns.

Preferably, the flow channel includes first and second flow cell end zones, disposed to extend through from first and second ends of the flow cell recess, the first and second flow cell end zones respectively having an entrance orifice and an exit orifice at distal ends thereof.

Preferably, the flow cell block is formed from elastic material.

Preferably, the elastic material is at least one selected from a rubber, an elastomer, and polydimethylsiloxane.

Furthermore, a flow cell lid is secured to the flow cell block, for covering the entrance orifice and the exit orifice. Slits are formed in the flow cell lid, positioned at the entrance orifice and the exit orifice, and openable when deformed elastically.

Preferably, the sample is constituted by first and second samples. A first sample fluid is caused through the flow channel to flow on the sensing surface to immobilize the first sample on the sensing surface. Then a second sample fluid is caused through the flow channel to flow on the sensing surface to assay interaction between the first and second samples according to contact between the first and second samples on the sensing surface.

Preferably, there are plural sensor cells each of which is constituted by the sensing surface and the flow channel.

Preferably, the thin film is a film of metal, and generates surface plasmon resonance on the sensing surface in response to incidence of the illuminating light.

Preferably, the first inner surface has a horizontal width of approximately 1 mm.

According to another aspect of the invention, an assay method of assay in utilizing attenuated total reflection is provided, in which a transparent dielectric medium, a thin film and a flow cell block are used, the thin film having a first surface and a sensing surface, the first surface being connected with the dielectric medium to constitute an interface, the sensing surface being back to the first surface, for detecting reaction of a sample, the flow cell block having a flow channel for flowing of the sample to the sensing surface, wherein illuminating light is applied through the dielectric medium to the interface to satisfy a total reflection condition, and a reflection angle upon occurrence of the attenuated total reflection of the illuminating light changes according to reaction of the sample on the sensing surface. The sample is passed to flow between the sensing surface and a first inner surface of the flow channel disposed opposite to the sensing surface to extend along, the first inner surface having a height, defined with reference to the sensing surface, and equal to or more than 200 microns, and equal to or less than 500 microns.

Consequently, the flow channel can be constructed for assay with high precision according to the invention, because the dimensions are suitably conditioned.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

Figure 1A:
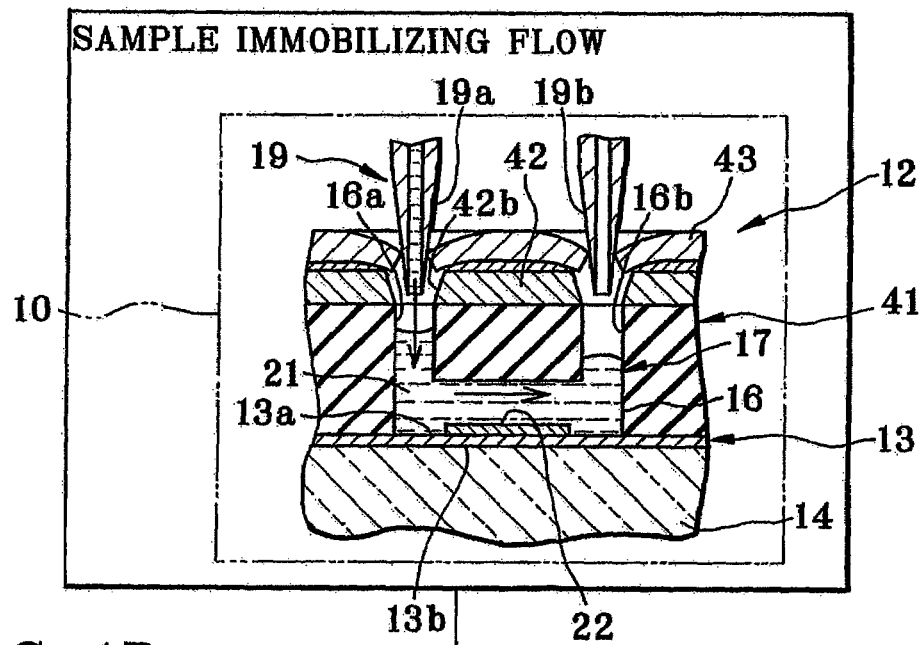
FIG. 1A is an explanatory view in section, illustrating a process of a sample immobilizing flow.

In FIG. 1, a surface plasmon resonance (SPR) assay system is schematically illustrated. The assay system includes a sample immobilizing device 10, an assay apparatus 11 and a data analyzer. The sample immobilizing device 10 introduces fluid of ligand toward a sensing surface for the purpose of immobilizing the ligand. The assay apparatus 11 assays interaction between the ligand and an analyte introduced after the ligand immobilization. The data analyzer is provided with data from the assay apparatus 11, and analyzes the data.

Elements in a sensor unit 12 are referred to. The sensor unit 12 includes a prism 14 as a dielectric element, a thin film 13 of metal and a multi channel flow cell block 41. The prism 14 is overlaid with the thin film 13 on which biomaterial for assay is positioned. The flow cell block 41 includes a flow channel 16, which causes fluid of the biomaterial, namely ligand and analyte, to flow on to the thin film 13. A thin film/dielectric interface 13b is defined between the prism 14 and the thin film 13, and constitutes one thin film surface that is reverse to a sensing surface 13a of the thin film 13.

An example of material for the thin film 13 is gold (Au) or the like. A thickness of the thin film 13 is 50 nm. The thickness can be changed for the suitability in view of the material of the thin film 13, a wavelength of light to be applied, and the like. The prism 14 is a transparent dielectric block, and overlaid with the thin film 13. Illuminating light is condensed by the prism 14 for application to the interface 13b to satisfy the total reflection condition. The flow channels 16 are in the U shape. Ends of the flow channels 16 respectively include an entrance orifice 16a and an exit orifice 16b. The entrance orifice 16a receives introduction of a sample fluid. The exit orifice 16b is accessed for draining the sample fluid.

A lower side of the flow channels 16 where the flow cell recess is open is enclosed by the prism 14 having the sensing surface 13a. There are defined sensor cells 17 each of which is a portion of the sensing surface 13a closed by the portion about the recess. In the present embodiment, the sensor unit 12 has plural sensor cells 17, for example three. See FIG. 3.

A sample immobilizing flow is for binding of ligand on the sensing surface 13a. At first, the sensor unit 12 is set in the sample immobilizing device 10. A pipetting type of fluid dispenser 19 is included in the sample immobilizing device 10, and has a dispensing pipette tip 19a and a removing pipette tip 19b. The dispensing pipette tip 19a is set at the entrance orifice 16a. The removing pipette tip 19b is set at the exit orifice 16b. The dispensing pipette tip 19a introduces fluid to the flow channel 16. The removing pipette tip 19b sucks and removes fluid from the flow channel 16. The introduction with the dispensing pipette tip 19a is at the same time as the removal with the removing pipette tip 19b. Ligand fluid 21 as sample fluid, as a fluid which contains ligand or biomaterial and fluid medium, is introduced through the entrance orifice 16a by the fluid dispenser 19.

An immobilizing linker film 22 is overlaid on the thin film 13 at the center of the sensing surface 13a. The linker film 22 is previously produced in the course of manufacturing the sensor unit 12. As the linker film 22 is a basis for immobilizing the ligand, various materials are available for selective use according to the type of the ligand to be immobilized.

In the sample immobilizing device 10, pre-treatment before a ligand immobilizing flow with the ligand fluid 21 is wetting of the linker film 22 by use of liquid buffer, and activation of the linker film 22 for the purpose of facilitating binding of the ligand to the linker film 22. An example of an immobilizing method is the amine coupling method. An example of material for the linker film is carboxy methyl dextran, to bind an amino group contained in the ligand with the dextran directly by a covalent bond. An example of liquid for the activation is mixture of N'-(3-dimethylaminopropyl) carbodiimide hydrochloride (EDC) and N-hydroxy imide succinate (NHS). The sample immobilizing device 10, after the activation, introduces liquid buffer for the ligand immobilizing flow to wash and clean the flow channel 16.

Various liquids are available for use as the liquid buffer for the ligand immobilizing flow, and solvent or diluent for the ligand fluid 21. Examples of the liquids include buffer liquids, or physiological saline water and other aqueous solutions of physiological salts, and pure water. It is possible according to a type of the ligand to determine suitably solution types and pH values of the solutions, and types of substances to be mixed, and their density. If a biomaterial is used as a ligand, physiological saline water is used of which pH value is kept neutralized. In the amine coupling method described above, the linker film 22 is electrified negatively because of the carboxy methyl dextran. In consideration of this, it is possible to use phosphatic buffered saline (PBS) solution having strong operation of buffer and containing phosphate salt at high density which is not physiological, because protein can be electrified positively for the purpose of facilitating binding with the linker film 22.

The sample immobilizing device 10, after the activation and washing, introduces the ligand fluid 21 to the flow channel 16 for immobilization. Ligand 21a as sample such as biomaterial diffused in the ligand fluid 21, in introducing the ligand fluid 21, gradually migrates to and binds with the linker film 22. This is the ligand immobilizing flow of the ligand 21a on the sensing surface 13a. It is general that a step of the immobilization requires approximately one (1) hour, during which the sensor unit 12 is preserved in an environment conditioned suitably, for example at a conditioned temperature. Until the immobilization, the ligand fluid 21 in the flow channel 16 may be left to stand in a stationary state. However, the ligand fluid 21 can be preferably stirred or turbulently flowed for ensured fluidity in the flow channel 16. The stirring or turbulent flow can promote binding of the ligand 21a with the linker film 22, to raise an immobilized amount of the ligand 21a.

When the immobilization of the ligand 21a on the sensing surface 13a is completed, the sample immobilizing device 10 removes the ligand fluid 21 from the flow channel 16. Namely, the removing pipette tip 19b discharges the ligand fluid 21 by suction. After this, the sensing surface 13a is washed by introducing washing liquid into the flow channel 16. In the sample immobilizing device 10, a blocking step is made after the washing. A blocking liquid is introduced into the flow channel 16, to deactivate the reaction group remaining without binding with the ligand. A preferable example of the blocking liquid is ethanol amine hydrochloride. After the blocking, the flow channel 16 is washed again. The sample immobilizing device 10 introduces evaporation retardant to the flow channel 16 after the final washing. The sensor unit 12 is left to stand until the assay, with the sensing surface 13a humid on the evaporation retardant.

For the assay, the sensor unit 12 is set in the assay apparatus 11. A pipetting type of fluid dispenser 26 is installed in the assay apparatus 11, and structurally the same as the fluid dispenser 19 in the sample immobilizing device 10. The fluid dispenser 26 introduces fluid to the flow channel 16 through the entrance orifice 16a. For the assay in the assay apparatus 11, at first, liquid buffer is introduced into the flow channel 16, and caused to flow continuously for a prescribed time. After this, analyte solution or analyte fluid 27, as a fluid which contains analyte and fluid medium that may be solvent, is introduced into the flow channel 16. Then liquid buffer is introduced again. Note that the flow channel 16 may be cleaned or washed before initially introducing the liquid buffer. Reading of data in a photo detector starts upon initially introducing the liquid buffer in order to detect a reference level of a signal. The reading is continued until the introduction of the liquid buffer at the second time after entry of analyte fluid 27. It is possible not only to detect the reference level that is a base line, but to assay interaction or reaction between the analyte and the ligand, and to measure a signal until dissociation between the analyte and ligand in response to introduction of the liquid buffer.

In the assay process, the content in the flow channel 16 is changed over by substitution, from the buffer to the analyte fluid 27, and then from the analyte fluid 27 to buffer. To change over the fluids, there is no complete draining of an initial fluid. When the flow channel 16 is filled with the analyte fluid 27, a buffer is introduced forcibly toward a position of the analyte fluid 27. The analyte fluid 27 is discharged out of the flow channel 16 by pressure of the introduced buffer, so as to complete the substitution of the fluids.

Various liquids are available for use as the liquid buffer for assay, and solvent or diluent for the analyte fluid 27. Examples of the liquids include buffer liquids, or physiological saline water and other aqueous solutions of physiological salts, and pure water. It is possible according to a type of a ligand or analyte to determine suitably solution types and pH values of the solutions, and types of substances to be mixed, and their density. To facilitate dissolving of the analyte, dimethyl sulfo-oxide (DMSO) can be added to the physiological saline water. The use of the DMSO considerably influences to a level of an output signal. The buffer for assay is used for detecting the reference level of the signal, as described above. If DMSO is contained in the fluid for the analyte, it is preferable to use buffer for assay at a DMSO density approximately equal to that of the fluid in the analyte.

In general, the analyte fluid 27 may be kept preserved for a long time, for example one (1) year. It is likely that a difference occurs between an initial level and a current level of the DMSO density owing to a change with time. If assay with high precision is required, such a difference in the density is estimated according to the reference signal (ref-signal) level upon introducing the analyte fluid 27, so that measured data can be compensated for by DMSO density compensation.

The reference signal or ref-signal is an output of the SPR derived from the reference region on the sensing surface 13a and free from immobilization of a ligand, and is a basis of comparison with a measuring signal. The measuring signal or act-signal is an output of the SPR derived from the measuring region on the sensing surface 13a and for immobilization of a ligand to react with an analyte. The data analyzer effects data analysis by obtaining a difference or ratio of the act-signal and ref-signal output by the assay apparatus 11. For example, the data analyzer obtains data of a finite difference between the act-signal and ref-signal, and analyzes various items according to the finite difference. This makes it possible to cancel electric noise caused by external irregularities, such as individual specificity of the sensor unit 12 or the linker film 22, mechanical changes of the assay apparatus 11, temperature changes of the liquid, and the like. A signal with a high S/N ratio can be obtained.

Compensation data for the DMSO density compensation is obtained before introducing the analyte fluid 27. A plurality of liquid buffers different in the DMSO density are introduced to the sensor cells 17. Amounts of changes in the levels of ref-signal and act-signal are evaluated so as to obtain the compensation data.

The optical assay unit 31 is constituted by the illuminator 32 and a photo detector 33. The reaction between the ligand and analyte can be recognized as a change of a resonance angle, which is an angle of incidence of light received by the interface 13b. To this end, the illuminator 32 is caused to apply light to the interface 13b at various values of angles of incidence satisfying a condition of the total reflection. The illuminator 32 includes a light source device 34 and an optical system 36, which includes a condensing lens, a diffusing plate and a polarizer. A position and angle of the installation of those elements are so determined that an angle of incidence of the light satisfies the condition of the above total reflection.

Examples of the light source device 34 include a light emitting diode (LED), laser diode (LD), super luminescent diode (SLD), and other light emitting element. A single element is used as the light source device 34 as a point light source, to illuminate the interface 13b in a sensor cell. Note that, if simultaneous assay of plural sensor cells is desired, light from a single light source device may be separated into plural light paths for application to the sensor cells. Alternatively, a plurality of light source devices may be arranged for association with respectively the sensor cells.

The diffusing plate diffuses light from the light source device 34, and suppresses onset of irregularity in the light amount. The polarizer allows only p-polarized light to pass, the p-polarized light creating the surface plasmon resonance. Note that no polarizer is required if directions of rays emitted by the light source device 34, for example an LD, are kept equal. However, a diffusing plate may be combined with the light source device 34 of a type of which directions of emitted rays are kept equal. Directions of rays in polarization are changed to an unequal state by the passage through the diffusing plate. For this structure, the polarizer can be utilized to set equal the directions of the rays. The light obtained after the diffusion and polarization is condensed by a condensing lens, and directed to the prism 14. It is possible to travel rays with various angles of incidence toward the interface 13b without irregularity in the intensity.

The photo detector 33 receives light reflected by the interface 13b of the thin film 13, and detects intensity of the light. Rays of light are incident upon the interface 13b at various angles. The light is reflected by the interface 13b at various angles of reflection according to the angles of the incidence. The photo detector 33 receives the light at various angles of the reflection. When the analyte fluid is introduced to the sensing surface 13a, a resonance angle changes according to interaction between the analyte and the ligand. A reflection angle of attenuation of the light also changes.

An example of the photo detector 33 is a CCD area sensor or an array of photo diodes, which receives light reflected by the interface 13b at various angles of reflection, and photo-electrically converts the light into an output of SPR. The interaction between the ligand and analyte is recognized as information of shifting of a position of attenuation of the reflected light on the photo reception surface of the photo detector 33. A refractive index of the thin film with the sensing surface 13a of the linker film becomes different between the states before and after the contact of the ligand with the analyte. Thus the resonance angle at which surface plasmon resonance occurs changes between those states. When reaction starts by the contact between the analyte and ligand, the resonance angle starts changes, to start shifting the attenuation position of the reflected light on the photo reception surface. The photo detector 33 outputs and sends an SPR signal to the data analyzer. The data analyzer analyzes the SPR output from the assay apparatus 11, to recognize interaction between the analyte and ligand.

Figure 1B:
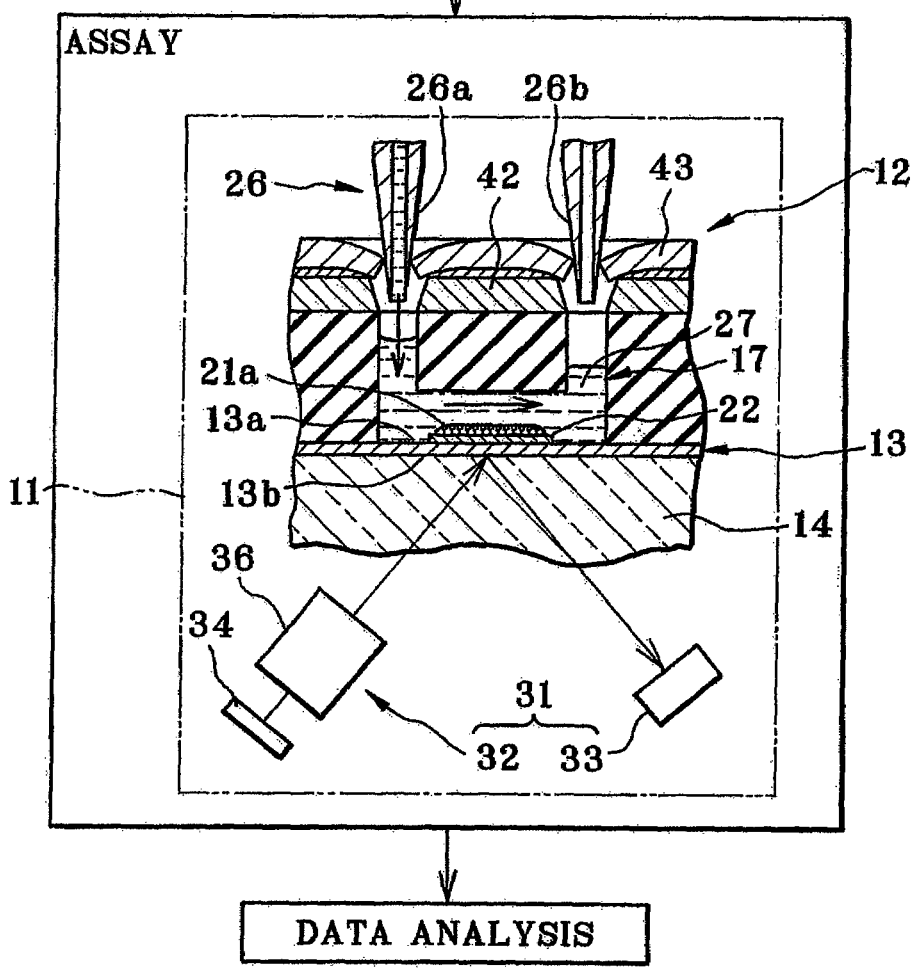
FIG. 1B is an explanatory view in section, illustrating processes of assay and data analysis.
Figure 2:
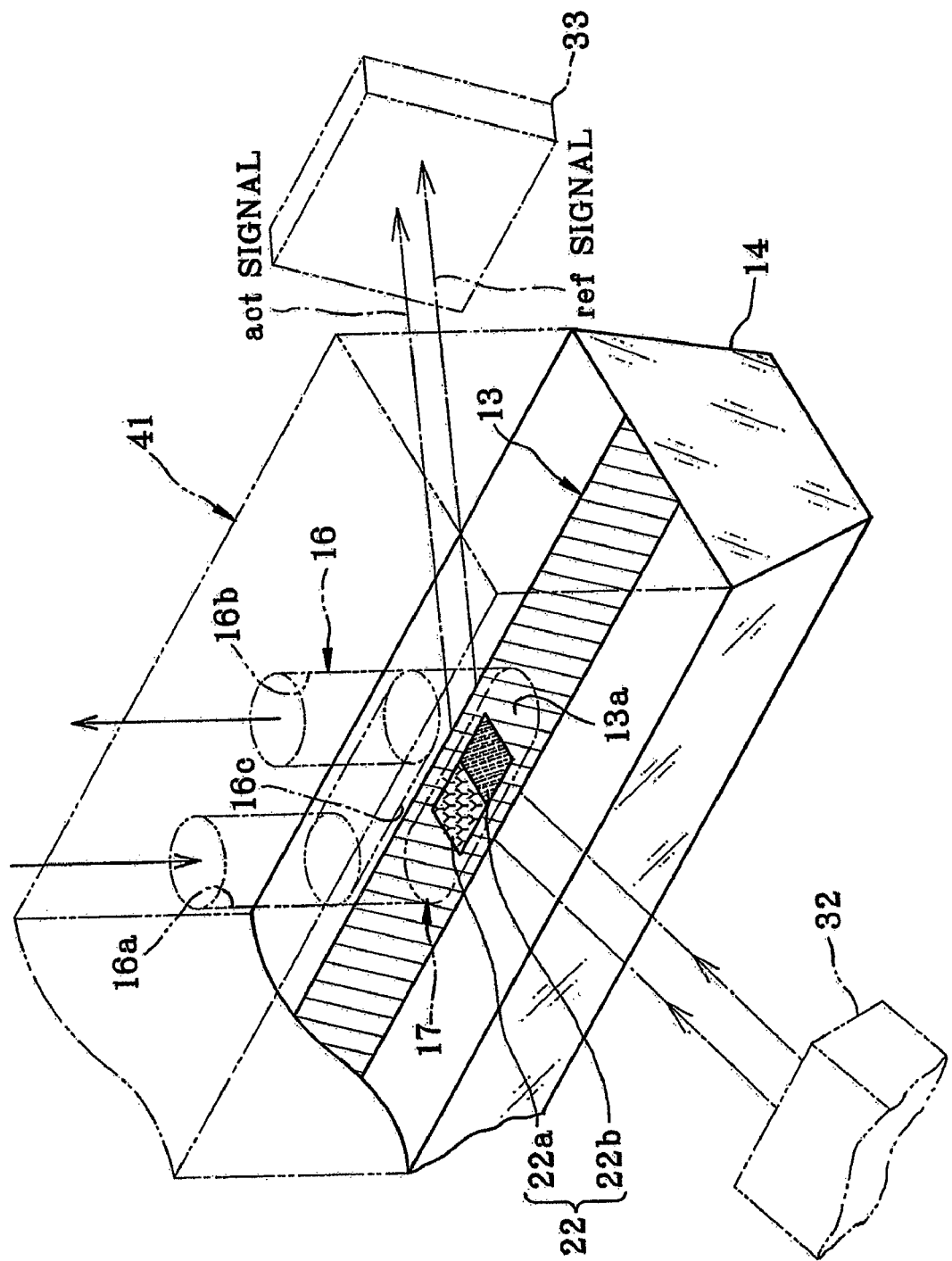
FIG. 2 is an explanatory view in a perspective view, illustrating measuring and reference regions on a sensing surface.

Note that in FIG. 2, the illuminator 32 and the photo detector 33 in the optical assay unit 31 are positioned so that a direction of light projected and reflected between those intersects horizontally with a flow of the flow channel 16, which is unlike the structure depicted in FIG. 1B. The state of FIG. 1B is simplified for the convenience. However, in the invention the illuminator 32 and the photo detector 33 may be positioned according to in FIG. 1B so that a direction of light projected and reflected between those is horizontally aligned with the flow of the flow channel 16 between the pipettes.

In FIG. 2 with the linker film 22, there are a measuring region 22a (act) and a reference region 22b (ref) formed in the linker film 22. The measuring region 22a has immobilization of a ligand, and is a region for reaction between the ligand and analyte. The reference region 22b does not have immobilization of a ligand, and is used for outputting a reference signal for comparison with a signal retrieved from the measuring region 22a. Note that the reference region 22b is formed in the course of film production of the linker film. An example of a process of the forming has steps of surface processing of the linker film 22 at first, and then deactivating the reaction groups in approximately a half of an entire area of the linker film 22 for binding with ligand. Thus, a half of the linker film 22 becomes the measuring region 22a. A remaining half of the linker film 22 becomes the reference region 22b.

The photo detector 33 outputs an act-signal for the measuring region 22a, and a ref-signal for the reference region 22b. The act-signal and ref-signal are simultaneously measured in a period between the detection of the reference level, association and dissociation. In the data analysis, a difference or ratio between the act-signal and ref-signal is calculated. For example, the data analyzer obtains measuring data of a finite difference between the act-signal and ref-signal, and analyzes the detection according to the finite difference data. It is possible to cancel electric noise caused by external irregularities, such as individual specificity of the sensor unit 12 or the linker film 22, mechanical changes of the assay apparatus 6, temperature changes of the liquid, and the like. Assay with high precision is possible.

The illuminator 32 and the photo detector 33 are constructed for measurement of two signal channels of the act-signal and ref-signal. To this end, a mirror for reflection is associated with the illuminator 32, for separating light from a single light-emitting element into plural light paths which are directed to the measuring and reference regions 22a and 22b. The photo detector 33 is constructed by photo diode arrays each of which is associated with one of the two signal channels, and receives the light on the light paths.

If a CCD area sensor is used as the photo detector 33, reflected light of the dual channels received at the same time can be recognized as an act-signal and ref-signal by the image processing. However, such a method according to the image processing might be too difficult. Alternatively, signals of the signal channels can be received by differentiating the time sequence for a very small period of time of the incidence between the measuring and reference regions 22a and 22b. An example of differentiating the time sequence is a use of a disk disposed on a light path and having two holes positioned at 180 degrees of a rotational angle. The disk is rotated to shift the time sequence between the signal channels. The holes are disposed at a difference of the radius from the rotational center in association with the interval between the measuring and reference regions 22a and 22b. When a first one of the holes enters the light path, illuminating light travels to the measuring region 22a. When a second one of the holes enters the light path, the light travels to the reference region 22b.

Figure 3:
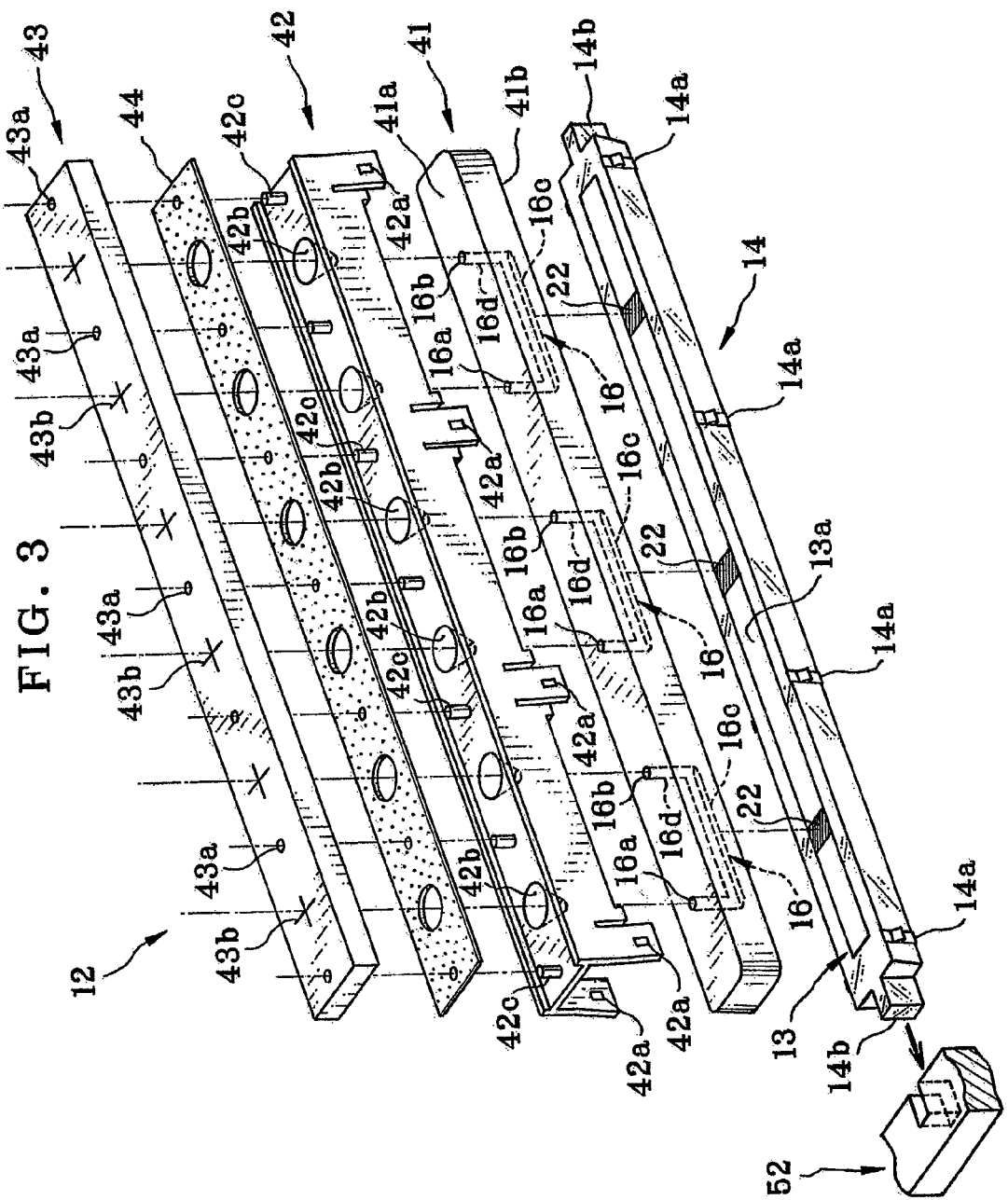
FIG. 3 is an exploded perspective view illustrating a sensor unit.

In FIG. 3, the sensor unit 12 is illustrated structurally. The sensor unit 12 includes the flow cell block 41, the prism 14, a flow cell fastener 42, and a flow cell lid 43. The flow cell block 41 has the three flow channels 16 formed through the same, or at least one flow channel. The prism 14 is dielectric, and is overlaid with the thin film 13 on its upper surface. The flow cell fastener 42 keeps the flow cell block 41 positioned by fitting its lower surface on the upper surface of the prism 14. The flow cell lid 43 is disposed higher than the flow cell fastener 42.

The thin film 13 is formed by vapor deposition on the prism 14. The thin film 13 of a strip shape is positioned on a train of the flow channels 16. Also, the linker film 22 is formed on the upper surface of the thin film 13 for the flow channels 16. Retention claws 14a are formed to project from the prism 14 at its sides as viewed longitudinally. Retention portions 42a of the flow cell fastener 42 are engageable with the retention claws 14a. The flow cell block 41 is sandwiched between the flow cell fastener 42 and the prism 14. A lower surface 41a of the flow cell block 41 is kept fitted on the prism 14. A unit including the flow cell block 41, the thin film 13 and the prism 14 is obtained.

Engageable projections 14b protrude from ends of the prism 14 as viewed in its longitudinal direction. In FIG. 3, a sensor holder 52 contains a plurality of sensor units 12 in the course of the sample immobilizing flow. The engageable projections 14b are formed for positioning the sensor unit 12 in a contained state by engagement with the sensor holder 52.

An access orifice 42b is formed in the flow cell fastener 42, and positioned at each of the entrance and exit orifices 16a and 16b of the flow channel 16, for entry of an end of each of the dispensing and removing pipette tips 19a and 19b, and a dispensing pipette tip 26a and a removing pipette tip 26b. The access orifice 42b has a funnel shape with a decreasing diameter for introducing liquid ejected by the pipette toward the entrance orifice 16a. A lower face of the access orifice 42b is connectable with the entrance and exit orifices 16a and 16b of the flow channel 16 for flow of fluid with the flow cell fastener 42.

Rod shaped bosses 42c are formed to project beside the access orifice 42b. Positioning holes 43a are formed in the flow cell lid 43. The bosses 42c are fitted in the positioning holes 43a, to position the flow cell lid 43 firmly. Double sided adhesive tape 44 attaches the flow cell lid 43 to an upper surface of the flow cell fastener 42. Note that suitable holes are formed in the double sided adhesive tape 44, and associated with the access orifice 42b and the bosses 42c.

The flow cell lid 43 covers the access orifice 42b communicating to the flow channel 16, and prevents evaporation of liquid in the flow channel 16. The flow cell lid 43 is formed from rubber, elastomer, resin or other elastic material. A cross shaped slit 43b is formed in the flow cell lid 43 and positioned respectively at the access orifice 42b. The flow cell lid 43 is required to cover the access orifice 42b in order to prevent liquid in the flow channel 16 from evaporation. However, no pipette can enter the access orifice 42b if covering of the flow cell lid 43 is complete. So the cross shaped slit 43b is formed to enable insertion of pipettes, and to close the access orifice 42b while no pipette is inserted. If a pipette is forcibly pressed into the cross shaped slit 43b, its edges are elastically deformed, to allow receipt of the pipette by becoming open. See FIGS. 1A and 1B. When the pipette is externally pulled out, the cross shaped slit 43b elastically closes the access orifice 42b again by returning to its initial state.

The flow cell block 41 is long in a strip shape, and includes the three flow channels 16 arranged in the longitudinal direction. The flow channels 16 have the U shape, and include a flow cell recess 16c with the first inner surface on a facing portion, and flow cell end zones or erect portions 16d. The flow cell recess 16c is formed in the lower surface 41a of the flow cell block 41, positioned opposite to the sensing surface 13a, and causes fluid to flow on the sensing surface 13a for its contact with the sensing surface 13a. Each of the flow cell end zones 16d has a first end connected with the entrance orifice 16a, and a second end constituted by the entrance or exit orifice 16a or 16b. The flow cell end zones 16d are erect from the flow cell recess 16c as bores formed through the flow cell block 41 vertically. Fluid introduced to the flow channel 16 through the entrance orifice 16a flows along the flow cell recess 16c for delivery to the sensing surface 13a.

Figure 4:
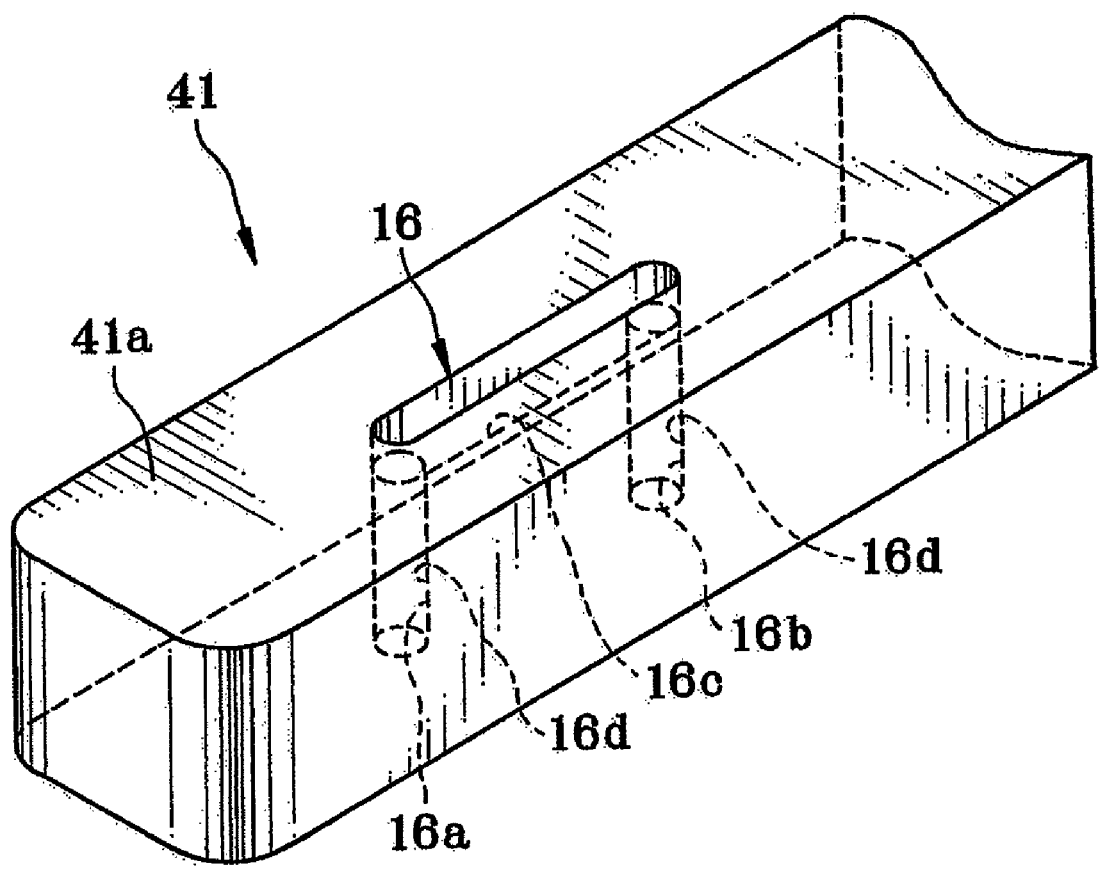
FIG. 4 is a bottom perspective view illustrating a flow channel.

In FIG. 4, the first inner surface is defined inside the flow cell recess 16c formed in the lower surface 41a. When the thin film 13 contacts the lower surface 41a, the recess is sealed in an enclosed manner with the sensing surface 13a. The flow channels 16 constitute the sensor cells 17 together with the thin film 13 in connection with its lower surface. See FIGS. 1A and 1B. The flow cell block 41 is formed from elastic material for the purpose of ensuring tightness in contact with the thin film 13. Examples of elastic materials include rubber, polydimethylsiloxane (PDMS), and the like. When the lower surface 41a of the flow cell block 41 is pressed on an upper surface of the prism 14, the flow cell block 41 is elastically deformed, to remove a space between its surface and the thin film 13. Open lower portions of the flow channels 16 are closed fluid-tightly by the upper surface of the prism 14.

Figure 5A:
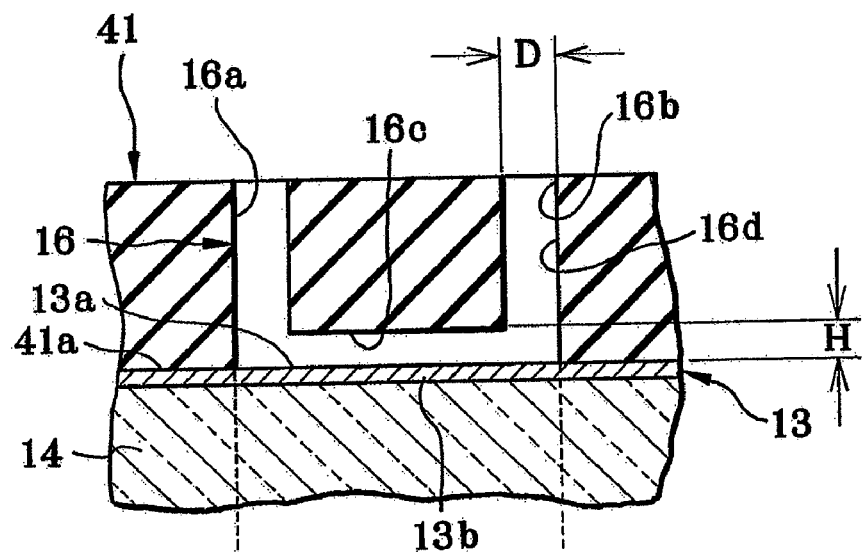
FIG. 5A is an explanatory view in a cross section, illustrating dimensions related to the flow channel.
Figure 5B:
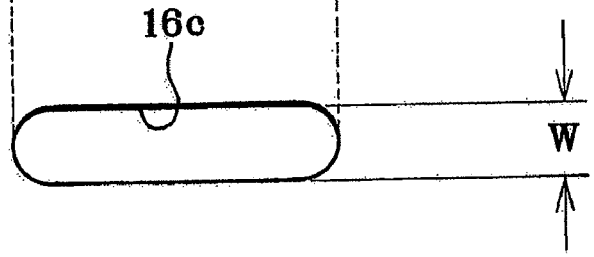
FIG. 5B is a top plan illustrating a retraction portion of the flow channel.

In FIGS. 5A and 5B, an interval between the entrance and exit orifices 16a and 16b of the flow channel 16 is approximately 10 mm. A diameter D of the flow cell end zones or erect portions 16d is approximately 0.7-0.8 mm. A horizontal width W or size of the flow cell recess 16c with the first inner surface on the facing portion is approximately 1 mm. A channel depth, or channel height H of the flow cell recess 16c from the sensing surface 13a to an upper surface of the flow cell recess 16c is approximately 0.3 mm. A volume of the space of the flow cell recess 16c is large according to the greatness of the channel height H, so that a great amount of ligand can be introduced, to increase an amount of an immobilized ligand on the sensing surface 13a.

Figure 6:
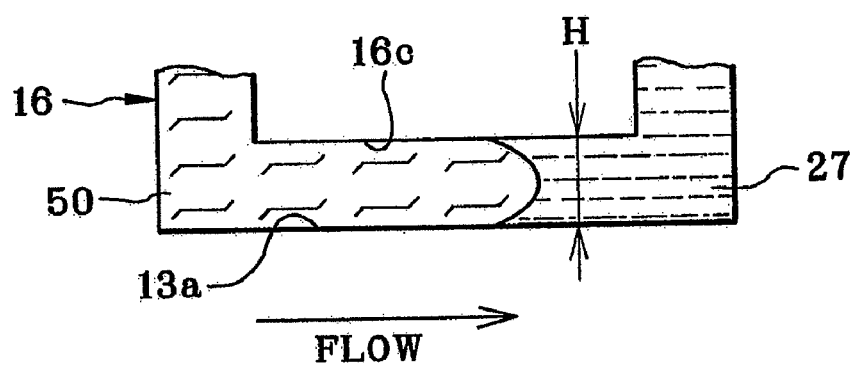
FIG. 6 is an explanatory view in a cross section, illustrating a gradient of a flow rate upon substitution of fluids.
Figure 7A:
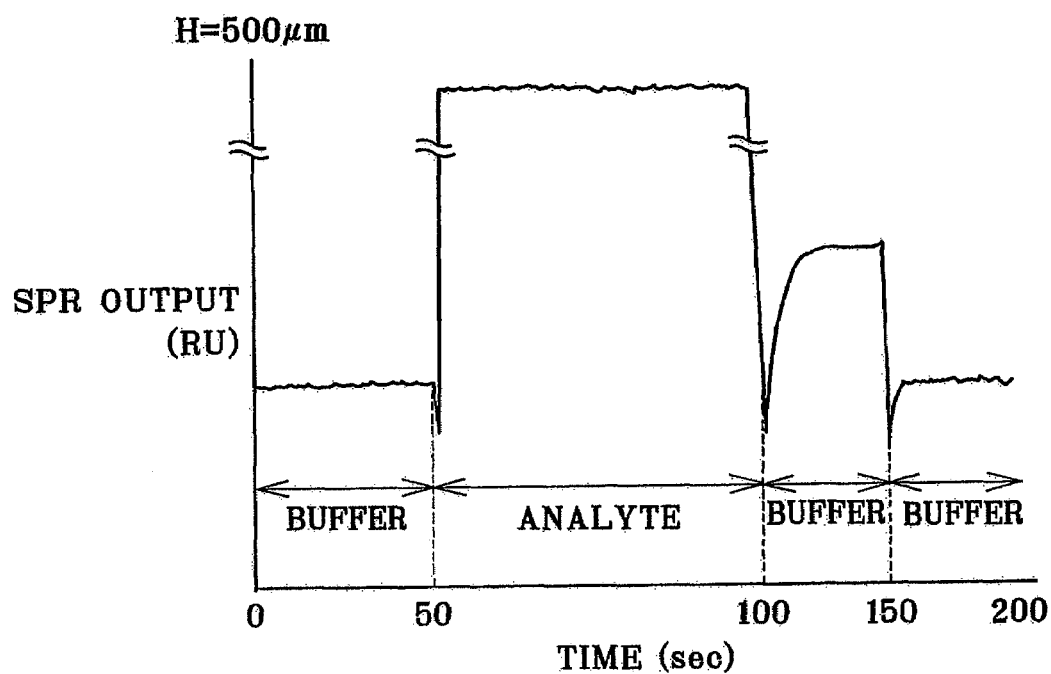
FIG. 7A is a graph illustrating a waveform of an output of the SPR in the assay.
Figure 7B:
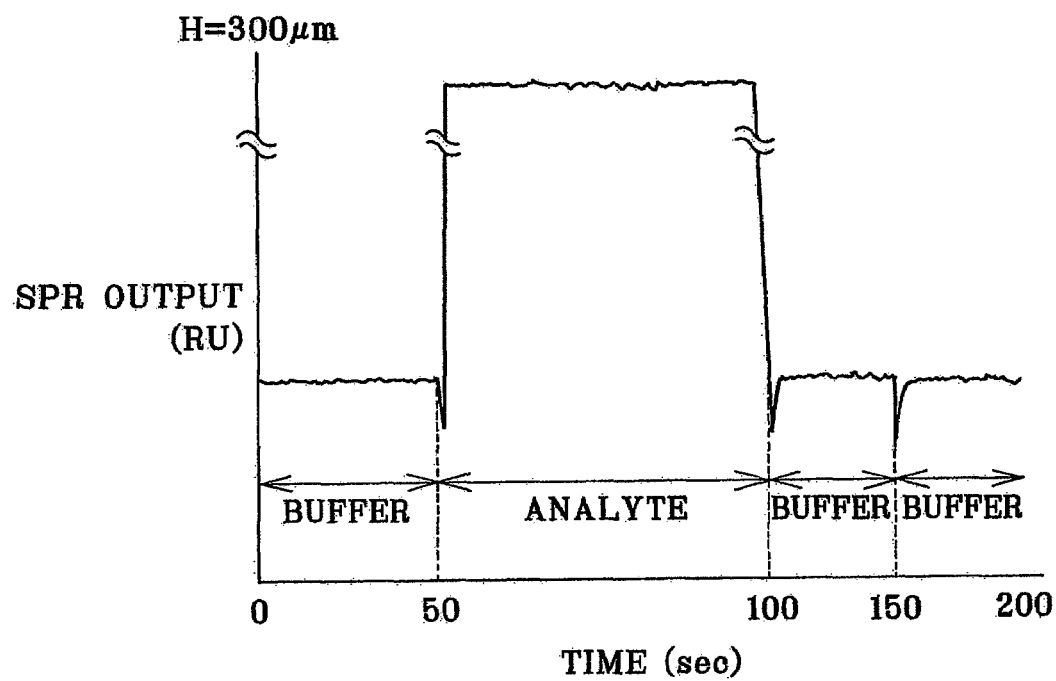
FIG. 7B is a graph illustrating a waveform of an output but under a condition different from FIG. 7A.

The channel depth, or channel height H, if smaller, is more favorable for the purpose of assay, which is in contrast with the sample immobilizing flow. In FIG. 6, a step prior to the dissociation of the analyte from the sensing surface 13a is depicted. The content of the flow channel 16 is changed over to a buffer liquid 50 from the analyte fluid 27 by substitution. The analyte fluid 27 in the flow cell recess 16c with the first inner surface, owing to its high viscosity, flows at a distribution of a flow rate with a gradient from the channel center toward the sensing surface 13a or the inner surface of the flow cell recess 16c. A local flow rate at the sensing surface 13a is lower than that at the channel center. The drop in the flow rate is smaller according to the smallness of the channel height H. The introduction of the buffer liquid 50 pushes the analyte from the sensing surface 13a, to minimize the remaining amount of the analyte. Thus, a high ratio of substitution of fluids can be obtained in a short time. In FIGS. 7A and 7B, signals of surface plasmon resonance in the course of measurement from the binding to the dissociation are depicted in graphs. According to FIG. 7A, signals are derived from the structure with the channel height H of 500 microns. According to FIG. 7B, signals are derived from the structure with the channel height H of 300 microns. A unit RU (resonance unit) is used for the signals of the SPR, and is an amount of a change in the attenuation angle according to a change in the refractive index on the sensing surface 13a. The value of the signal of the SPR is higher according to an amount of the change.

At first, the flow channel 16 is filled with the buffer liquid 50 to measure a base line of the output of the SPR. Then the analyte fluid 27 is introduced forcibly into the flow channel 16. The buffer liquid 50 is ejected to flow out by the analyte fluid 27, which contacts the sensing surface 13a in turn. Then binding between the ligand and analyte occurs on the sensing surface 13a, to raise a signal level of the output of the SPR. After this, the buffer liquid 50 is introduced forcibly into the flow channel 16. The analyte fluid 27 is ejected to flow out by the buffer liquid 50, which is stored in turn by substitution. Reaction of the dissociation is analyzed according to a measured signal upon substitution. As found in the graphs of FIGS. 7A and 7B, a signal level upon introduction of a buffer at one time is higher when the channel height H is 500 microns in FIG. 7A than when the channel height H is 300 microns in FIG. 7B. This means that a higher amount of the residual content of the analyte is found on the sensing surface 13a. The substitution of fluids is relatively slower. If the channel height H is 500 microns, the signal level comes back to the base line upon the second time of introducing the buffer. However, the delay in the substitution results in a drop of the precision in the measurement of a speed of reaction of the dissociation.

Figure 8:
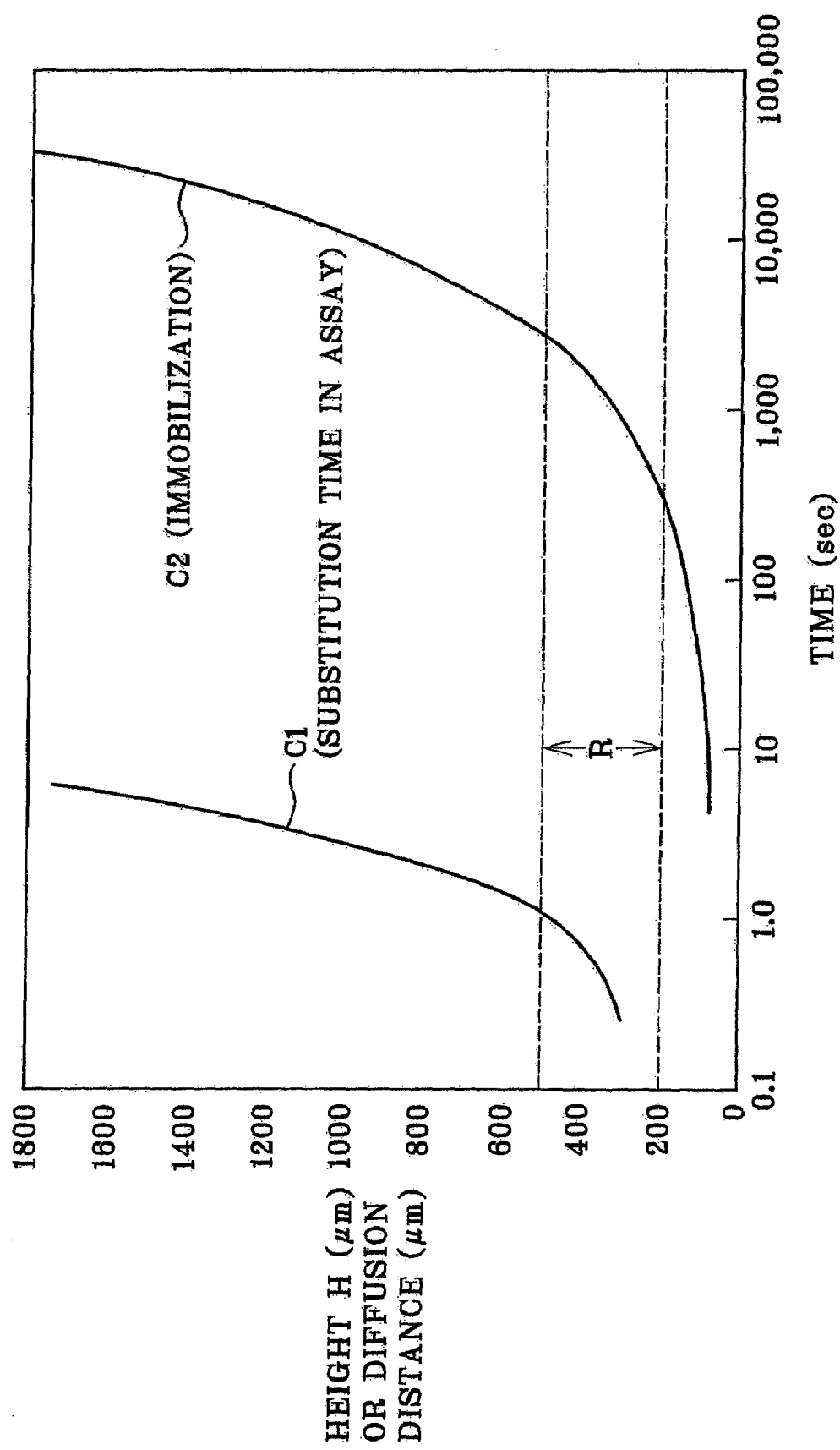
FIG. 8 is a graph illustrating a relationship between the channel height and time of substitution.

In FIG. 8, a curve C1 represents a relationship between the channel height H and the substitution time required for a reach to a predetermined ratio of substitution of liquids. An example of the ratio is 99.7% at the time of the assay. It is observed with the curve C1 that the substitution time is long according to the greatness of the channel height H, so as to slow down the assay of the interaction between the ligand and the analyte. So an upper limit of the channel height H is preferably 500 microns in consideration of a tolerant level of the precision in the assay. An upper limit is desirably 350 microns if a particularly high precision is intended. In contrast, it is observed that a quantity of an immobilized sample is smaller according to the smallness of the channel height H. So a lower limit of the channel height H is preferably 200 microns in consideration of a tolerant quantity of the immobilized sample in the assay. A lower limit is desirably 250 microns if a particularly sufficient quantity of an immobilized sample is intended. A range R of the channel height H for the purpose of balancing the precision in the assay and the acquisition of a sufficient immobilized sample is 200-500 microns, and desirably 250-350 microns.

A curve C2 represents a relationship between ligand immobilizing flow time and a diffusion distance of ligand during the ligand immobilizing flow. It is observed with the curve C2 that the diffusion distance of the ligand in the ligand fluid increases with a lapse of time. Namely, the ligand of a greater amount migrates to the sensing surface 13a with time. Consequently, a ratio of immobilization is found to increase according to a greater value of the ligand immobilizing flow time, the ratio being such of the immobilized ligand amount to an amount of introduced ligand fluid. Note that a molecular weight of the ligand is regarded as 50,000 in relation to the graph of FIG. 8.

Note that, in the sensor unit 12, the number of the flow channels 16 may not be three, but can be one or two, or four or more.

In the above embodiment, the sensor unit is a composite structure including the metal film, flow channel and prism. However, no prism may be included in a sensor unit. Instead, a prism can be included in a main unit of the assay apparatus. Furthermore, a sensor unit according to the invention may be different from that including the metal film and flow channel, for example, can be a chip type having a sensor chip. For use with a chip type of sensor, a flow channel is formed in an assay apparatus. A channel depth, or channel height H of the flow channel is determined according to the condition described heretofore.

In addition to the SPR sensor, an assay sensor unit according to the invention can be other sensor in utilizing attenuated total reflection. One example of sensor unit according to utilizing the attenuated total reflection is a leaky mode sensor. The leaky mode sensor includes a dielectric medium, a cladding layer overlaid on the dielectric medium, and an optical waveguide layer overlaid on the cladding layer, those layers constituting a thin film. A first surface of the thin film is a sensing surface on the optical waveguide layer. A second surface of the thin film is a metal/dielectric interface on the cladding layer. When light becomes incident on the metal/dielectric interface to satisfy the condition of the total reflection, part of the light passes through the cladding layer, and enters the optical waveguide layer. A guided mode to propagate light is excited responsively in the optical waveguide layer, to attenuate the reflected light on the metal/dielectric interface. An angle of the incidence at which the guided mode is excited is changeable according to the refractive index of the medium positioned on the sensing surface. This is similar to the characteristic of the resonance angle of the SPR sensor. The attenuation of the reflected light is detected, so that it possible to measure the interaction on the sensing surface.

Also, various techniques associated with the surface plasmon resonance (SPR) assay can be combined with the present invention in the field of the chemical or biochemical analysis.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A sensor unit for assay in utilizing attenuated total reflection, including a transparent dielectric medium, a thin film having a first surface and a sensing surface, said first surface being connected with said dielectric medium to constitute an interface, said sensing surface being back to said first surface, for detecting reaction of a sample, and a flow cell block having a flow channel for flowing of said sample to said sensing surface, wherein illuminating light is applied through said dielectric medium to said interface to satisfy a total reflection condition, and a reflection angle upon occurrence of said attenuated total reflection of said illuminating light changes according to reaction of said sample on said sensing surface, said sensor unit comprising:

wherein said flow channel comprises a facing portion, disposed opposite to said sensing surface to extend along, for passing said sample to flow between, an inner surface of said facing portion having a height, defined with reference to said sensing surface, and equal to or more than 200 microns, and equal to or less than 500 microns;

wherein an analyte fluid is introduced into said channel in which an buffer fluid is filled in assaying a reaction of binding of said sample, so as to substitute said analyte fluid for said buffer fluid in said flow channel;

wherein introducing of said analyte fluid is stopped while said reaction of binding is assayed.

2. An assay method of assay in utilizing attenuated total reflection, in which a transparent dielectric medium, a thin film and a flow cell block are used, said thin film having a first surface and a sensing surface, said first surface being connected with said dielectric medium to constitute an interface, said sensing surface being back to said first surface, for detecting reaction of a sample, said flow cell block having a flow channel for flowing of said sample to said sensing surface, wherein illuminating light is applied through said dielectric medium to said interface to satisfy a total reflection condition, and a reflection angle upon occurrence of said attenuated total reflection of said illuminating light changes according to reaction of said sample on said sensing surface, said assay method comprising a step of:

passing said sample to flow between said sensing surface and a facing portion of said flow channel disposed opposite to said sensing surface to extend along, an inner surface of said facing portion having a height, defined with reference to said sensing surface, and equal to or more than 200 microns, and equal to or less than 500 microns;

introducing an analyte fluid into said channel in which a buffer fluid is filled in assaying a reaction of binding of said sample, so as to substitute said said analyte fluid for said buffer fluid in said flow channel;

wherein introducing of said analyte fluid is stopped while said reaction of binding is assayed.

* * * * *